United States Patent
Jukic

(10) Patent No.: US 11,309,665 B1
(45) Date of Patent: Apr. 19, 2022

(54) ACTIVE CABLE ARRANGEMENT FOR CONNECTING MEDICAL DEVICES TO A DISPLAY

(71) Applicant: Vedran Jukic, Trieste (IT)

(72) Inventor: Vedran Jukic, Trieste (IT)

(73) Assignee: OSSI, Sudbury, MA (US)

( * ) Notice: Subject to any disclaimer, the term of this patent is extended or adjusted under 35 U.S.C. 154(b) by 225 days.

(21) Appl. No.: 16/789,965

(22) Filed: Feb. 13, 2020

Related U.S. Application Data

(60) Provisional application No. 62/804,838, filed on Feb. 13, 2019.

(51) Int. Cl.
*A61B 5/00* (2006.01)
*H01R 13/66* (2006.01)
*G06F 15/16* (2006.01)

(52) U.S. Cl.
CPC ....... *H01R 13/6691* (2013.01); *A61B 5/0022* (2013.01); *G06F 15/16* (2013.01); *H01R 2201/06* (2013.01)

(58) Field of Classification Search
None
See application file for complete search history.

(56) References Cited

U.S. PATENT DOCUMENTS

| | | | | |
|---|---|---|---|---|
| 10,637,930 B2 * | 4/2020 | Heinz | ............ | G16H 40/67 |
| 2010/0318699 A1 * | 12/2010 | Gao-Saari | ............ | G16H 40/40 |
| | | | | 710/72 |

FOREIGN PATENT DOCUMENTS

WO  WO-2015105612 A1 *  7/2015 ............. A61B 5/002

* cited by examiner

*Primary Examiner* — Kristy A Haupt
(74) *Attorney, Agent, or Firm* — Michael Razavi; Alfred F. Hoyte, Jr.

(57) ABSTRACT

A customized active dongle plus cable arrangement is used to show combined and time synchronized data from different medical devices in realtime or from a specified point in time on a connected medical grade standard display monitor. The active cable arrangement of the invention is capable of communicating with a plurality of legacy and third-party medical devices via their designed physical and proprietary semantic protocols. Using the active cable arrangement, the user has the sensation of "plug and play", by simply connecting the medical device to the monitor USB port (or to the USB hub extending the monitor USB port). The active cable arrangement of the invention transforms the proprietary protocol of the medical device, providing the monitor with standardized output for data, waveforms, alarms, setting, notifications, values and other useful information. The standard medical grade display monitor will support the display of such information according to the software API and specifications of the normalized JSON protocol.

8 Claims, 4 Drawing Sheets

ACTIVE CABLE ARRANGEMENT FOR CONNECTING MEDICAL DEVICES TO A DISPLAY

CROSS REFERENCE TO RELATED APPLICATIONS

This application is claims the benefit of Provisional Patent Application No. 62/804,838 filed Feb. 13, 2019.

FIELD OF THE INVENTION

This application relates to healthcare facility data management hardware and software, and more particularly to reliable medical device data display in a standardized format useful for healthcare facility functioning and medical research.

BACKGROUND OF THE INVENTION

Modern hospitals are complex, technologically sophisticated organizations having sometimes thousands of employees, doctors, nurses, medical technicians and administrators, with critical life or death decisions being made regularly and sometimes having to be made abruptly and quickly. Up-to-date, perspicuous, and complete data about the patient is desirable. And even when critical decisions are not at stake, increases in the cost of health care have made it imperative to use patient data, facility personnel and resources as efficiently as possible.

Hospitals and other healthcare facilities providing surgical services must coordinate a myriad of resources, medical personnel, and hospital staff to provide optimum and efficient care to their patients. Patient data collected during operations, other medical procedures and patient recovery is updated continually and often needs to be displayed immediately and in an efficient and speedily apprehended manner to attending medical personnel as well. The patient data is permanently retained in a standard format useful for facility management and medical researchers among others who may be in remote locations and/or need to compare data from myriad healthcare facilities.

In typical hospital settings such an operating room, ICU, recovery room etc., there are multiple medical devices surrounding a patient. For convenient, efficient assessment of the data collected and to control these devices, it is helpful to have their associated data displayed on a single monitor to have all the relevant information on a "single piece of glass". To achieve this, typically, a medical gateway (typically a general purpose PC computer) is setup to receive data from all the surrounding devices, convert the data to a standard format, synchronize it, and arrange for its display on a monitor proximate. But general purpose PCs, despite being commonplace, are actually an exceedingly varied and complex group of devices, each needing a specific setup and configuration, and ongoing maintenance of both software and hardware to maintain system security and efficiency. Simply put, the maintenance of general purpose PCs dedicated to data display ends up being a substantial expense for hospitals.

Biondi et al, U.S. Pat. No. 8,886,792B2, and Gao-Saari et al, U.S. Pat. No. 8,225,015B2, show the complexity and criticality of providing an integrated display from multiple heterogeneous medical devices in various circumstances, but provides no simple, stable, inexpensive solution for any specific hospital setting.

In contrast to previous, wide-spread, conventional attempts to solve the problems of long-term reliable, secure connections to multiple heterogeneous medical devices and combining the displays of the data they produce for efficient apprehension, the instant invention provides a simple, stress-free, inexpensive connection and data-combining scheme requiring no special effort or consideration on the part of the medical personnel attempting to care for patients in a wide range of hospital settings.

SUMMARY OF THE INVENTION

In accordance with the present disclosure, embodiments of a system, method, and apparatus are described which eliminate or ameliorate the problems and disadvantages associated with previous systems, methods, and apparatuses.

In an embodiment of the apparatus, a customized active cable arrangement is provided having at one end, a connector designed to mate with a specific medical device which transmits digital data that may be in a proprietary format, through said connector. At its other end, said cable arrangement is provided with a second connector, typically of a standard type, such as USB, PoE (Power Over Ethernet) for connecting with a supporting standard monitor for display. Said cable arrangement is also provided with a powered processing capability which has been preprogrammed such that the cable arrangement converts the data format of said medical device to a conventional format used by said standard monitor and transmits to the monitor the data for display in real-time as well as for permanent recording by a medical facility information system. The cable arrangement of the invention is based upon the possibilities of a modern standard medical display featuring multiple USB connectivity and ability to render images from HTML5 (SVG and JAVASCRIPT) sources. This technology is typically used in rendering WEB pages across modern smart-tv's, smartphones, and other devices designed to display information. The rendering display does not necessary have the full implementation of HTML5, but a minimal subset to successfully render information provided from adequate protocol.

In a particular embodiment, a plurality of such active cable arrangements are provided to connect a matching plurality of potentially different, proprietary medical devices to a single monitor wherein each cable arrangement converts the data format of the corresponding connected device, and all of the data streams of the devices are displayed in realtime simultaneously on said monitor. In a further variation, each active cable of said plurality connects, not directly to said monitor, but to a common dongle or interface device which plugs into said monitor creating a single display showing simultaneously time-synchronized data streams in graphical form from each of said plurality of medical devices.

Particular embodiments include a cable having an RS 232 connector, a USB connector, or a standard Ethernet RJ145 connector to mate with a medical device employing complementary connectors. In further variations, the cable arrangement can connect to the medical device wirelessly, employing a WiFi connection, a standard WiFi access point (AP) connection, or a standard bluetooth connection.

Particular embodiments include a cable arrangement which connects to a proprietary medical device via a supported third party Medical Gateway using a standard or proprietary connector.

DETAILED DESCRIPTION

Figure 1:
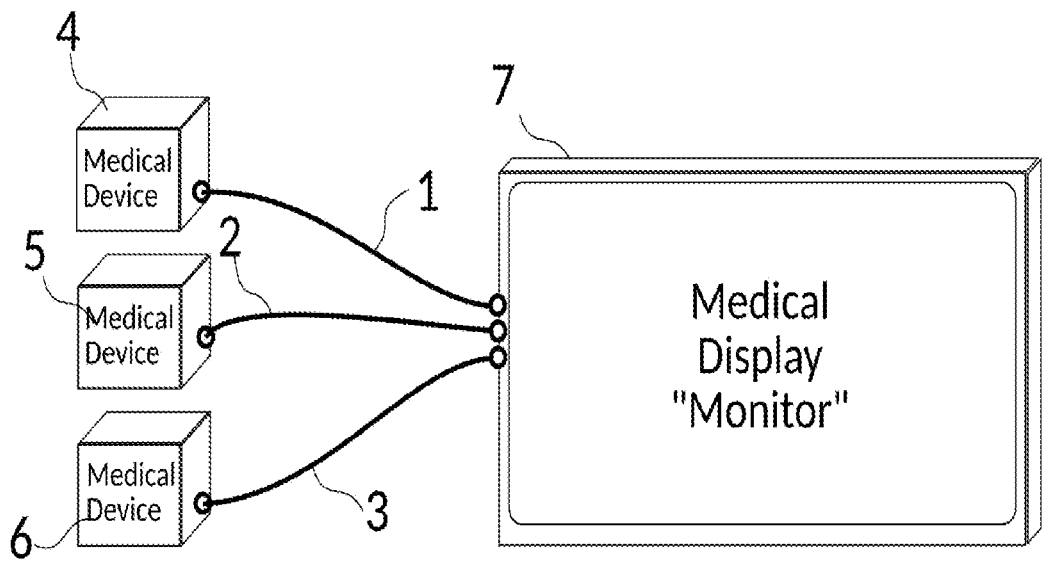
FIG. 1 is a block diagram of an embodiment of the invention wherein three active cables, each connected to a medical device, are plugged into a conventional monitor.

FIG. 1 is a block diagram overview of an embodiment of the invention. According to the invention, medical devices 4, 5 and 6 are connected using corresponding active cable arrangements 1, 2, and 3 to a conventional medical display monitor 7. Note that the term "active cable arrangement" and "active cable" are used herein to describe the programmable dongle 12 and associated connectors and cables as will be explained in more detail below. In the example shown, medical devices 4, 5, or 6 can take on many different forms. Example medical devices include patient monitoring devices, blood analyzers, infusion pumps, ventilators, mobile EKG units, glucose analyzers, incubators, or other devices. Typically, "legacy" or third party medical devices lack an ability to be seamlessly integrated with a health care or hospital information system. The medical devices 4, 5, and 6 may have proprietary connectors (i.e., output ports having a non-standard physical arrangement) and/or transmit data in a proprietary format. In accordance with one aspect of the invention, the active cabled, 2, and 3 of the invention are custom manufactured to order, both physically (if necessary) and with respect to the logic with which they are preprogrammed, for each corresponding medical device 4, 5, or 6. Thus, the user has the sensation of "plug and play" by simply connecting the medical device 4, 5, or 6 to an active cable 1, 2, or 3 of the invention to a conventional monitor USB port or USB hub extending the monitor USB port. The active dongle 12 of the invention is programmed to transform the proprietary data transmission protocol of the medical device 4, 5, or 6 and provide the monitor 7 (or other device) with standardized output for data, waveforms, alarms, setting, notifications, values and other useful information.

Instead of the general purpose processing capability of the usual intermediary PC or other intermediary electronic device, the active dongle 12 of the active cable arrangement of the invention has a dedicated, preprogrammed processing capability for transforming the data to a standard format for storage and display. The active dongle 12 is not easily susceptible to reprogramming or hacking. It is not expected that a software update would ever be required during the normal lifetime of the associated medical device as the data transmission protocol of the medical device 4, 5, or 6 will never change.

If a new medical device is added or replaces an older device, it is not necessary to install a new software driver on an intermediary PC (or equivalent), an uncertain prospect depending on the PC operating system, compatibility with other drivers/devices and many other details. Instead, along with placing into service a new medical device, a new active cable arrangement according to the invention is ordered and simply plugged in.

The supporting monitor 7 should support the display of the standardized and known, well documented values for data, waveforms, alarms, setting, notifications, values and other useful information from the USB dongle 12 of the invention, for example the software API and specifications of the normalized JSON protocol.

Prior to the invention, such medical devices 4, 5, or 6 would typically transmit data to an intermediary general purpose computer, for example, a conventional PC, for processing including display, analysis and recording. Such general purpose computers are commonplace and nominally inexpensive. But such PCs require continual maintenance including security and function upgrades. In well publicized incidents, computer hackers have halted or impeded the operations of health facilities, hospitals or entire health systems as a result of such intermediary PCs not having security upgrades implemented.

Figure 2:
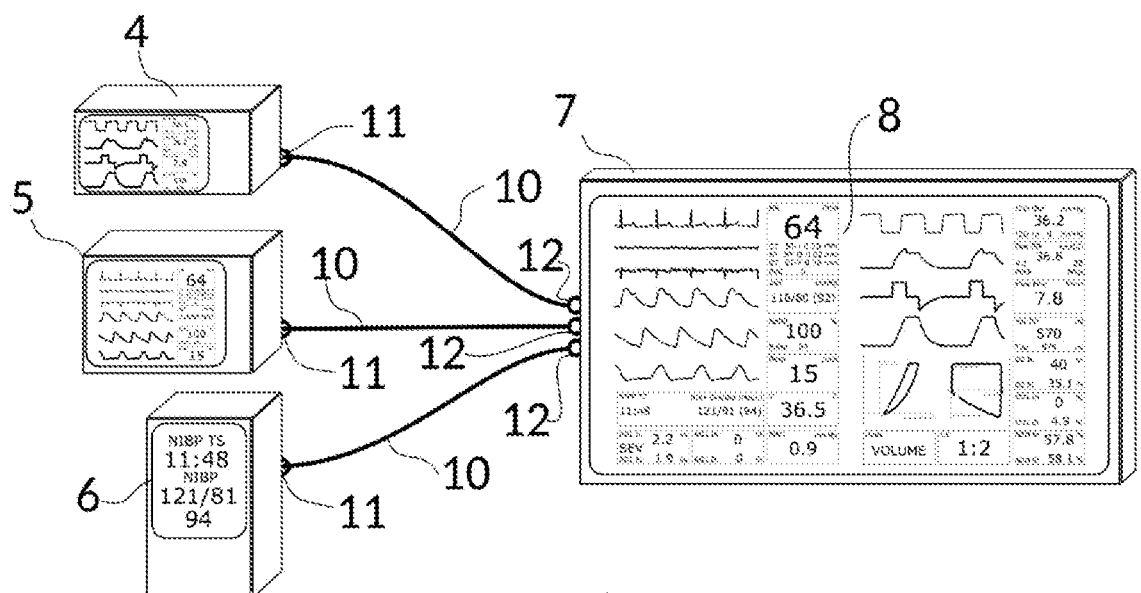
FIG. 2 illustrates the combined data displayed side-by-side and synchronously on a conventional medical monitor from three medical devices connected to the monitor with active cables in an embodiment of the invention.

FIG. 2 illustrates the same-glass, side-by-side (or vertically arranged) synchronized display of the data transmitted by medical devices 4, 5 and 6. It should be noted here that the data transmitted by the medical devices 4, 5, and 6 will be displayed simultaneously on the monitor 7 in real time, even though the devices will be plugged into separate inputs. Preferably, monitor 7 is a standard medical monitor utilizing the JSON protocol. In an embodiment, connecting cables 10 do not have customized processing capability although they are equipped with conventional or proprietary connectors suitable for corresponding connected devices 4, 5, and 6. Instead, cables 10 plug into USB dongles 12 to form the cable arrangements 1, 2, and 3 of the invention, with each having customized processing capability corresponding to each connected medical device. USB dongles 12 in turn plug into conventional medical monitor 7. USB dongles 12 process the data from corresponding connected medical devices 4, 5 and 6, synchronizing it and formatting it for display 8 on monitor 7. The use of USB to connect to the dongle 12 to monitors is advantageous because it provides power to the dongle 12.

The active dongle 12 and associated connecting cables are built from standard parts by the manufacturer for the ordered medical device. Building the active cable assemblies 1, 2, or 3 from parts involves selecting the right connector and protocol for the device 4, 5, or 6, which protocol is written to the dongle 12 in a manner well known to those of skill in the art and then assembled and shipped to the user. The manufacturer does not need a skilled workforce.

Figure 3:
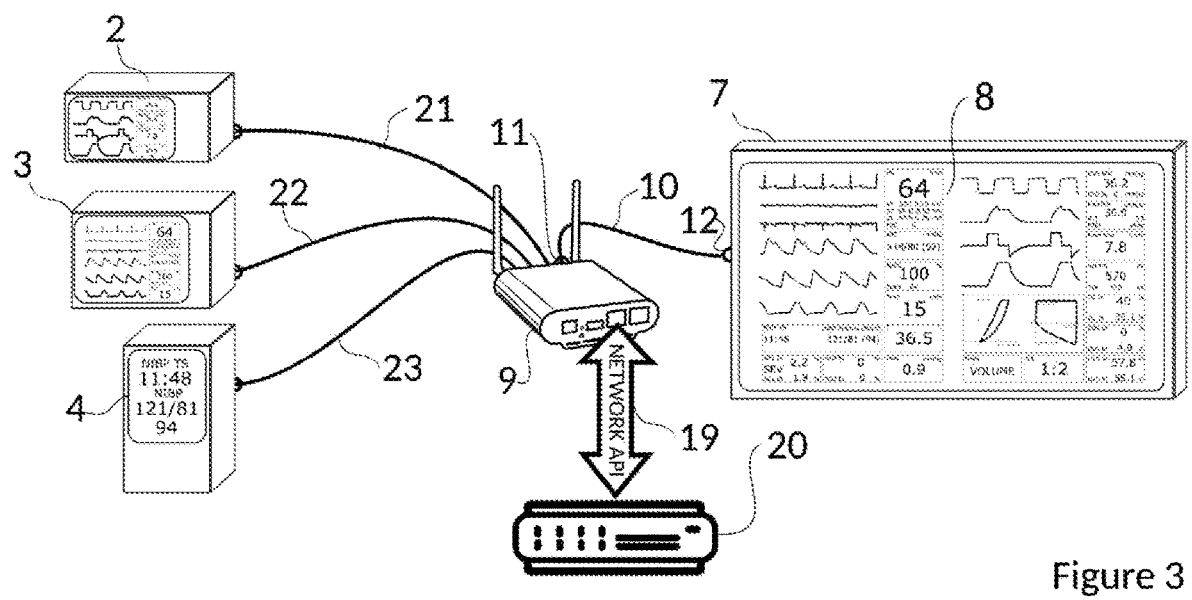
FIG. 3 is a diagram illustrating the connection of three medical devices with active cables to an IoT device enabling transmission of the medical device data to a remote server for permanent storage and/or analysis. The IoT device also passes through the data streams to a monitor for display.

An intermediary IoT Connectivity Device 9 is used to facilitate recording in an embodiment illustrated in FIG. 3. An IoT Connectivity Device is a hardware device that enables physical and logical data transformation from proprietary and non-standardized protocols, to be collected and transformed into a standardized dataset. It also serves as a security and functional layer around the medical devices. As it has all the protocols implemented locally, it does not suffer from data loss (i.e., does not need to be reprogrammed or booted up) if the network is temporarily or otherwise unavailable. It is equipped with a battery and can be unplugged for significant periods, such as during transfer, or unforeseen power outages such as accidental connector detachment or temporary power failure, with full operational readiness. An IoT device used in the medical environment must be compliant with regulations imposed by law (for example with IEC EN 60601-1). TCP and UDP protocols and ports are used.

Ordinary cables 22, 23 and 24 connect medical devices such as 4, and for the purposes of FIG. 3 only, 2 and 3, to device 9. The device 9 formats the data for recording and uses Network API 19 to transmit the data to Hospital Information System 20. One should appreciate that the hospital information system 20 has a number of roles or responsibilities with respect to medical devices. One responsibility of the hospital information system 20 includes coordinating or managing activities of medical devices. The data formatted for display is then transmitted to conventional monitor 7 for display 8 via cable arrangement 1, 2, or 3 with optional USB dongle 12.

For example, in a hospital operating room (OR) during a typical 24 hours, patient monitors, anesthesia machines or ventilators, EEG monitoring, a BIS monitor and a few IV pumps will typically create 1 GB of data with perhaps a 60-85% compression ratio, resulting in a 150-400 MB encrypted repository for complete, high frequency datasets, including waveforms. For an average 10 hours of OR usage per day, and 24 Hours ICU Monitor per patient, the 24 hours encrypted, and compressed storage are expected to be in 80-120 MB range per bedside location.

Figure 4:
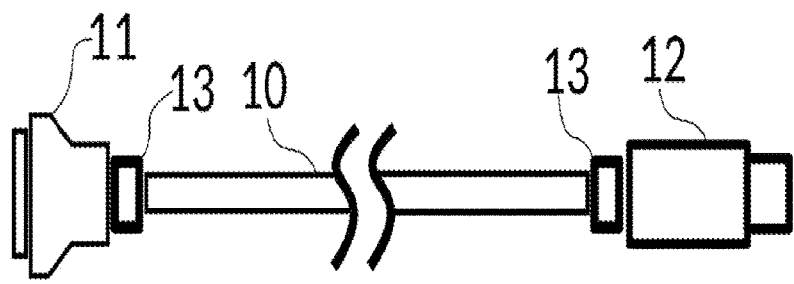
FIG. 4 is a block diagram showing the details of the physical construction of an active cable arrangement in an embodiment.

FIG. 4 is a block diagram illustrating the physical construction of the active cable arrangement of the invention in an embodiment. The active cables 1, 2, or 3 are manufactured to order for a specific, medical device such as 4, 5 or 6. Connector 11 may be standard or proprietary, specific to said device 4, 5, or 6. Connector 11 plugs into or otherwise connects to a standard RJ45 connector 13 which terminates both ends of a standard Cat 5 or Cat 6 Ethernet cable 10. The connector 13 opposite from said medical device 4, 5, or 6 plugs into USB dongle 12 which contains the processing capability and customized preprogrammed logic necessary to format for synchronized display data from said medical device. USB dongle 12 is powered by standard electrical output from the monitor 7 to which it is connected.

Figure 5:
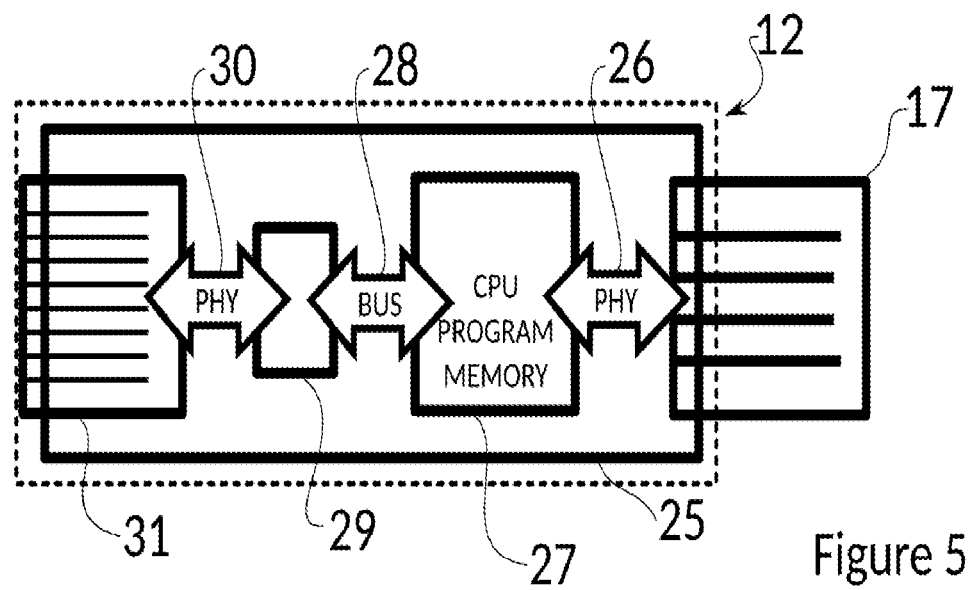
FIG. 5 is a block diagram illustrating the details of the logical processing capability of an active cable arrangement in an embodiment.

FIG. 5 is a block diagram illustrating the logical construction of the USB dongle 12 in an embodiment. Processor 27 receives power through USB standard connector 17 by which, dongle 12 is plugged into a monitor. Processing unit 29 receives data via medical device connector 31, converts proprietary data format to JSON key-value pairs, communicates using this standard format over bus 28 to processor 27 which synchronizes the data and otherwise prepares it for recording and display. As mentioned above, monitor 7 is a standard medical monitor and will automatically display the reformatted data from medical devices 4, 5, or 6 as standalone or in a combined time synchronized manner. The data from medical devices 4, 5, or 6 is not just displayable on monitor 7, it is transformed so as to be useable for any device. For example, data from device 4, 5, or 6 may be transmitted to hospital information center 20.

Figure 6:
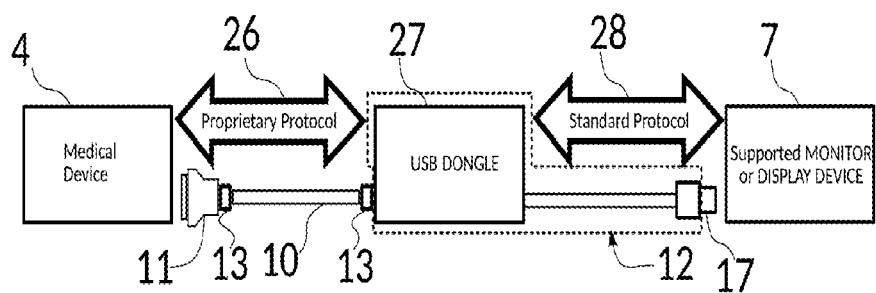
FIG. 6 is a block diagram illustrating the overall system and processing sequence in an embodiment.

FIG. 6 is a block diagram illustrating the cable arrangement and overall system in an embodiment. USB dongle 12 is connected to medical device 4 via a cable constructed as described in the description associated with FIG. 4 hereinabove. Dongle 12, a programmable microprocessor driven interface device, communicates with device 4 via proprietary protocol 26, uses its preprogramed logic to process the data into a standard format, and then transmits the processed data to monitor 7 using a standard protocol 28.

Figure 7:
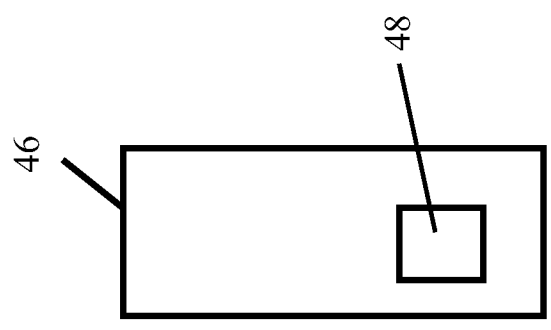
FIG. 7 is a graphical representation of the method of the invention in an embodiment illustrating the interconnection of the various computing resources necessary to produce the active cable arrangement of the invention.
Figure 7:
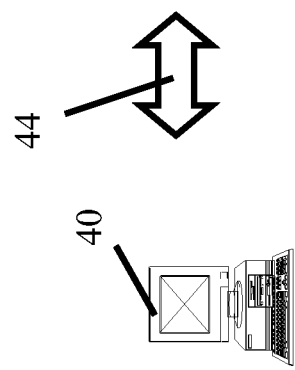

In another embodiment, the invention provides an automated method for providing a connecting cable arrangement 1, 2, or 3 for connecting a legacy or third party medical device such as 4, 5, or 6 having a proprietary connection arrangement or data transmission protocol (or both) to a standard medical monitor, from a manufacturer to an end user. In a preferred embodiment the method is implemented by way of a secure internet transaction. FIG. 7 shows a diagram representing principal equipment and key actions involved in a common internet purchasing transaction. A customer computing device 40 such as a PC, smart phone, tablet, or other device is operated by a user (not illustrated), for example, a person using his or her home or office computer. The customer has internet access via WiFi, or equivalent allowing the customer to communicate over the internet 44 to a large number of web sites. The customer accesses web sites of interest using the computing device 40. One web site is represented by a manufacturer 46 of the inventive active cable arrangement, the web site having data processing equipment including a server 48 for processing and saving data. Server 48 includes a database of known legacy medical devices. In accordance with the method, the end user would select a device of interest from a "drop down" list, a list of representative GUIs, or other means of displaying identifying information representing a list of medical devices/products stored on server 48. For each medical device listed, its transmission protocol and connection arrangement is known and stored on the server 48 but transparent to the user. The list is generated by the server 48 and can be transmitted over the internet 44 to the user for display on the user device 40 in response to a user request. If the user sees the desired medical device on the list he/she simply "clicks" on the device displayed on the list. Preferably, an actual image of the device (with the physical arrangement of the device output connector apparent) is stored on the server 48 and displayed in response to the click and the user can verify that the model selected is indeed the desired model. The user may then complete the transaction in the well known manner. Using the saved data regarding the selected device on server 48, which saved data will include the particular transmission protocol as well as the details of the particular connection arrangement of the selected legacy medical device, the manufacturer 46 will then provide or fabricate all of the cables and connectors necessary as discussed above, and program the dongle 12 with the appropriate software to generate an active cable arrangement such as 1, 2, or 3. The arrangement is then shipped to the user, who can then connect the medical device 4, 5, or 6 to the monitor 7 in "plug and play" fashion. The user need not further configure or program the cable arrangement or monitor 7.

If the user's desired medical device 4, 5, or 6 is not saved in the server 48 database, the user would provide either a specific model number and/or other information necessary for the manufacturer to determine the physical characteristics of the medical device connector as well as the data transmission protocol of the device. It should be noted that the above method is not limited to the examples shown, but can be used to retrofit any legacy or non-standard device for connectivity.

The invention could be used not only for display devices, but in general for any device, regulated medical devices as well, to receive standardized medical data from supported medical devices, if latter is equipped with standard USB connectivity and ability to read a standard protocol provided.

Although particular embodiments have been described in this disclosure, many other variations and modifications will be apparent to those skilled in the art. Thus, the instant invention can be defined and limited only by the claims to be associated with this application.

The invention claimed is:

1. A method of providing a customized active cable arrangement for connecting a particular medical device to a standard medical monitor, said particular medical device having at least a proprietary connection arrangement or proprietary data transmission protocol, in response to a user request, said request generated by a computing device, said request transmitted to a remote server associated with a manufacturer over a network, the method comprising the steps of:
providing said server with a database of medical device data, said database including a list of medical devices, each medical device on said list having particular identifying information associated therewith;
presenting said list of medical devices on said computing device in response to said user request and allowing a user to select a medical device on said list having particular identifying information matching identifying information associated with said medical device; and, configuring said customized active cable arrangement.

2. The method of claim 1 wherein configuring said customized cable arrangement comprises the step of providing a connector and attached cable, said connector compatible with said proprietary connection arrangement.

3. The method of claim 1 wherein configuring said customized cable arrangement comprises the step of providing a preprogrammed interface, said interface programmed to convert said proprietary transmission protocol to a standard protocol.

4. The method of claim 3 wherein configuring said customized cable arrangement comprises the step of providing an output connector for said interface.

5. The method of claim 4 wherein said output connector is a USB connector.

6. The method of claim 1 comprising the further step of storing data regarding proprietary transmission protocols for each of said medical devices listed on said server.

7. The method of claim 1 comprising the further step of storing data on said server regarding proprietary connection arrangements for each of said medical devices listed on said server.

8. The method of claim 1 comprising the further step of storing image data on said server corresponding to each medical device listed on said server.

* * * * *